US 6,660,678 B1

(12) United States Patent
Liu

(10) Patent No.: US 6,660,678 B1
(45) Date of Patent: Dec. 9, 2003

(54) SINGLE-SITE CATALYSTS FOR OLEFIN POLYMERIZATION

(75) Inventor: Jia-Chu Liu, Mason, OH (US)

(73) Assignee: Equistar Chemicals, LP, Houston, TX (US)

( * ) Notice: Subject to any disclaimer, the term of this patent is extended or adjusted under 35 U.S.C. 154(b) by 513 days.

(21) Appl. No.: 09/716,954

(22) Filed: Nov. 21, 2000

(51) Int. Cl.[7] .................................................. B01J 31/00
(52) U.S. Cl. ....................... 502/152; 502/103; 502/117; 502/118; 526/160; 526/943; 526/161
(58) Field of Search ................................ 502/152, 103, 502/117, 118; 526/160, 943, 161

(56) References Cited

U.S. PATENT DOCUMENTS

| | | | |
|---|---|---|---|
| 5,153,157 A | 10/1992 | Hlatky et al. ................ | 502/117 |
| 5,198,401 A | 3/1993 | Turner et al. ................ | 502/155 |
| 5,241,025 A | 8/1993 | Hlatky et al. ................ | 526/129 |
| 5,539,124 A | * 7/1996 | Etherton et al. ............. | 548/402 |
| 5,554,775 A | 9/1996 | Krishnamurti et al. ......... | 556/7 |
| 5,624,878 A | 4/1997 | Devore et al. ............... | 502/152 |
| 5,637,660 A | 6/1997 | Nagy et al. .................. | 526/160 |
| 5,902,866 A | 5/1999 | Nagy et al. .................. | 526/133 |

OTHER PUBLICATIONS

J. March, *Advanced Organic Chemistry*, 2d Ed. (1977), pp. 1054–1055.

* cited by examiner

Primary Examiner—Ling-Siu Choi
(74) Attorney, Agent, or Firm—Jonathan L. Schuchardt

(57) ABSTRACT

A method for making single-site catalysts useful for olefin polymerization is disclosed. A nitrogen-functional heterocycle is first deprotonated with an alkyllithium compound, followed by reaction of this anionic ligand precursor with about 0.5 equivalents of a Group 4 transition metal tetrahalide in a hydrocarbon solvent at a temperature greater than about 10° C. to give an organometallic complex-containing mixture. When combined with exceptionally low levels of an activator (e.g., methyl alumoxane), the mixture actively polymerizes olefins to give polymers with a favorable balance of physical properties, including low density and narrow molecular weight distribution.

15 Claims, No Drawings

SINGLE-SITE CATALYSTS FOR OLEFIN POLYMERIZATION

FIELD OF THE INVENTION

The invention relates to catalysts useful for olefin polymerization. In particular, the invention relates to an improved method for preparing "single-site" catalysts based on heterocyclic ligands such as carbazolyl and quinolinoxy ligands.

BACKGROUND OF THE INVENTION

While Ziegler-Natta catalysts are a mainstay for polyolefin manufacture, single-site (metallocene and non-metallocene) catalysts represent the industry's future. These catalysts are often more reactive than Ziegler-Natta catalysts, and they produce polymers with improved physical properties. The improved properties include narrow molecular weight distribution, reduced low molecular weight extractables, enhanced incorporation of α-olefin comonomers, lower polymer density, controlled content and distribution of long-chain branching, and modified melt rheology and relaxation characteristics.

Metallocenes commonly include one or more cyclopentadienyl groups, but many other ligands have been used. Putting substituents on the cyclopentadienyl ring, for example, changes the geometry and electronic character of the active site. Thus, a catalyst structure can be fine-tuned to give polymers with desirable properties. "Constrained geometry" or "open architecture" catalysts have been described (see, e.g., U.S. Pat. No. 5,624,878). Bridging ligands in these catalysts lock in a single, well-defined active site for olefin complexation and chain growth.

Other known single-site catalysts replace cyclopentadienyl groups with one or more heteroatomic ring ligands such as boraaryl (see, e.g., U.S. Pat. No. 5,554,775 or azaborolinyl groups (U.S. Pat. No. 5,902,866).

U.S. Pat. No. 5,539,124 (hereinafter "the '124 patent") and U.S. Pat. No. 5,637,660 teach the use of anionic, nitrogen-functional heterocyclic groups such as indolyl, carbazolyl, 2-pyridinoxy or 8-quinolinoxy as ligands for single-site catalysts. These ligands, which are produced by simple deprotonation of inexpensive and readily available precursors, are easily incorporated into a wide variety of transition metal complexes. When used with common activators such as alumoxanes, these catalysts polymerize olefins to give products with narrow molecular weight distributions that are characteristic of single-site catalysis.

One drawback of the catalysts described above is their relatively low activity. Normally, a large proportion of an alumoxane activator must be used to give even a low-activity catalyst system. For example, in the '124 patent, Example 16, a bis(carbazolyl)zirconium complex is used in combination with methylalumoxane at an aluminum:zirconium mole ratio [Al:Zr] of 8890 to 1 to give a catalyst having a marginally satisfactory activity of 134 kg polymer produced per gram Zr per hour. In Example 22, a similar complex is used with less activator (i.e., [Al:Zr/h]=1956 to 1) to give a catalyst with an activity of only 10 kg/g Zr/h. The activator is expensive, and when it is used at such high levels, it represents a large proportion of the cost of the catalyst system. Ideally, much less activator would be needed to give a catalyst system with better activity.

Another drawback relates to polymer properties. While the '124 patent teaches that catalysts made by its method give polymers with "a narrow molecular weight distribution," the actual molecular weight distributions of polymers made with the bis(carbazolyl)zirconium dichloride catalysts of Examples 16 and 22 of this reference are not reported. In fact, the molecular weight distributions of these polymers would preferably be narrower. I found that the MWDs of polymers made using the '124 catalysts are actually greater than 3 (see Comparative Examples 6–8 and 11–13, below).

In sum, there is a continuing need for single-site catalysts that can be prepared inexpensively and in short order from easy-to-handle starting materials and reagents. In particular, there is a need for catalysts that have good activities even at low activator levels. Ideally, the catalysts would produce, at low activator levels, polyolefins with desirable physical properties such as good comonomer incorporation, favorable melt-flow characteristics, and narrow molecular weight distributions.

SUMMARY OF THE INVENTION

The invention is a method for making single-site catalysts useful for olefin polymerization. The method comprises two steps. First, a nitrogen-functional heterocycle is deprotonated with an alkyllithium compound to produce an anionic ligand precursor. The heterocycle is an indole, carbazole, 8-quinolinol, 2-pyridinol, or a mixture thereof. In the second step, the anionic ligand precursor reacts with about 0.5 equivalents of a Group 4 transition metal tetrahalide (or with about 1 equivalent of an indenyl Group 4 transition metal trihalide) in a hydrocarbon solvent at a temperature greater than about 10° C. to give a mixture that contains the desired organometallic complex.

Catalyst systems comprising the organometallic complex-containing mixtures and an activator, as well as olefin polymerization processes that use the catalyst systems, are also included.

The complex-containing mixture actively polymerizes olefins, even when used with an exceptionally low level of an activator. Solvent dilution further enhances catalyst activity. In addition, the resulting polymers have a favorable balance of physical properties, including narrow MWD. The method provides a simple route to a variety of heterocycle-based, single-site catalysts and reduces the overall cost of these systems by reducing the amount of costly activator needed for high activity.

DETAILED DESCRIPTION OF THE INVENTION

Catalyst systems prepared by the method of the invention comprise an activator and an organometallic complex-containing mixture. The catalysts are "single site" in nature, i.e., they are distinct chemical species rather than mixtures of different species. They typically give polyolefins with characteristically narrow molecular weight distributions (Mw/Mn<3) and good, uniform comonomer incorporation.

The organometallic complex-containing mixture includes a complex that contains a Group 4 transition metal, M, i.e., titanium, zirconium, or hafnium. Preferred complexes include titanium or zirconium. The mixture also normally includes unreacted starting materials and lithium halides.

In one aspect, the invention is a method for preparing the organometallic complex-containing mixture. The method comprises two steps: deprotonation of the ligand, and reaction of the anionic ligand precursor with a Group 4 transition metal tetrahalide.

In the first step, a nitrogen-functional heterocycle is deprotonated with an alkyllithium compound. Suitable nitrogen-functional heterocycles are indoles, carbazoles, 8-quinolinols, and 2-pyridinols. These compounds can have substituents that do not interfere with deprotonation or the subsequent reaction with the transition metal halide. Many of these compounds are commercially available or are easily synthesized. For example, indole, carbazole, 8-quinolinol, and 2-pyridinol are all inexpensive and commercially available, and many indoles are easily made from arylhydrazones of aldehydes or ketones and a Lewis acid using the well-known Fischer indole synthesis (see J. March, *Advanced Organic Chemistry,* 2d ed. (1977), pp. 1054–1055, and references cited therein). Additional examples of suitable nitrogen-functional heterocycles are described in U.S. Pat. Nos. 5,637,660 and 5,539,124, the teachings of which are incorporated herein by reference.

An alkyllithium compound is used to deprotonate the nitrogen-functional heterocycle. Suitable alkyllithium compounds can be made by reacting lithium with an alkyl halide. More often, they are purchased as solutions in a hydrocarbon (e.g., toluene or hexanes) or ether (e.g., diethyl ether or tetrahydrofuran) solvent. Preferred alkyllithium compounds are $C_1$–$C_8$ alkyllithiums such as methyllithium, isopropyllithium, n-butyllithium, or t-butyllithium. n-Butyllithium is particularly preferred because it is readily available, relatively easy to handle, and effective.

Usually, equimolar amounts of the alkyllithium compound and the nitrogen-functional heterocycle are used to produce the anionic precursor. Deprotonation can be performed at any suitable temperature, preferably at or below room temperature. While the deprotonation reaction can be performed at temperatures as low as −78° C. or below, it is preferred to perform this step at room temperature. Vigorous mixing is essential because the lithium salt of the anionic ligand tends to precipitate and forms a thick slurry. The reaction is usually complete within an hour or two. The resulting anionic ligand precursor includes a carbazolyl, indolyl, 8-quinolinoxy, or 2-pyridinoxy anion and a lithium cation.

In the second step, the anionic ligand precursor reacts with a Group 4 transition metal tetrahalide. Suitable Group 4 transition metal tetrahalides include zirconium, titanium, or hafnium, and four halide groups, which may the the same or different. Suitable tetrahalides include, for example, zirconium tetrachloride, dibromozirconium dichloride, titanium tetrabromide, zirconium tetraiodide, hafnium tetrachloride, and the like, and mixtures thereof. Zirconium tetrachloride and titanium tetrachloride are preferred.

Reaction of about 0.5 equivalents of the Group 4 transition metal tetrahalide with one equivalent of the anionic ligand precursor gives an organometallic complex-containing mixture that includes the desired bis(carbazolyl), bis(indolyl), bis(2-pyridinoxy) or bis(8-quinolinoxy) complex. The reaction is performed at temperature greater than about 10° C., which is not only convenient, but gives the best results. Preferably, the reaction occurs at a temperature within the range of about 15° C. to about 60° C.; most preferably, the reaction is simply performed at room temperature. The reaction is usually complete within a few hours, but it is often convenient and desirable to allow the reaction to proceed overnight (about 16–18 hours) at room temperature.

The preparation of the organometallic complex-containing mixture is performed in the presence of a hydrocarbon solvent. Preferred hydrocarbons are aromatic, aliphatic, and cycloaliphatic hydrocarbons having from 4 to 30 carbons, preferably 4 to 12 carbons, because these are conveniently removed from the mixture. Examples include pentanes, hexanes, cyclohexane, octanes, toluene, xylenes, and the like, and mixtures thereof.

When the reaction is complete, the mixture is preferably just concentrated by solvent removal under a stream of nitrogen or with vacuum stripping to give a solid residue that contains the desired organometallic complex in addition to some unreacted starting materials and some lithium halide salt as a by-product. This mixture commonly contains as much as 50 wt. % of recovered starting material (e.g., carbazole). Nonetheless, this residue is well-suited for use "as is" in a subsequent olefin polymerization. Also suitable, although less desirable, is to filter a solution of the organometallic complex-containing mixture to remove insoluble by-products.

Preferred organometallic complexes have the general structure $LL'MX_2$, wherein M is zirconium or titanium, X is a halogen, and each of L and L', which may be the same or different, is selected from the group consisting of indolyl, carbazolyl, 8-quinolinoxy, and 2-pyridinoxy. More preferably, X is Cl or Br.

In a second method of the invention, the anionic ligand precursor is instead reacted with about one equivalent of an indenyl Group 4 transition metal trihalide under the conditions described above. The indenyl Group 4 transition metal trihalide is conveniently made according to well-known methods by reacting an indenyl anion with a Group 4 transition metal tetrahalide. The indenyl anion is produced by deprotonating indene with a potent base such as an alkyllithium compound or a Grignard reagent. Examples 28–30 below illustrate the second method.

Organometallic complex-containing mixtures of the invention are normally combined with an activator when they are used to polymerize olefins. As illustrated below in Example 2, the activator is commonly mixed with the complex just prior to use as a catalyst.

Suitable activators are well known in the art. Examples include alumoxanes (methyl alumoxane (MAO or PMAO), modified methyl alumoxane (MMAO), ethyl alumoxane, diisobutyl alumoxane), alkylaluminum compounds (triethylaluminum, diethyl aluminum chloride, trimethylaluminum, triisobutyl aluminum), and the like. Suitable activators include acid salts that contain non-nucleophilic anions. These compounds generally consist of bulky ligands attached to boron or aluminum. Examples include lithium tetrakis(penta-fluorophenyl)borate, lithium tetrakis(pentafluorophenyl)aluminate, anilinium tetrakis (pentafluorophenyl)borate, and the like. Suitable activators also include organoboranes, which include boron and one or more alkyl, aryl, or aralkyl groups. Suitable activators include substituted and unsubstituted trialkyl and triarylboranes such as tris(pentafluorophenyl)borane, triphenylborane, tri-n-octylborane, and the like. These and other suitable boron-containing activators are described in U.S. Pat. Nos. 5,153,157, 5,198,401, and 5,241,025, the teachings of which are incorporated herein by reference. Alumoxanes are particularly preferred activators; methyl alumoxane is most preferred.

The amount of activator needed relative to the amount of organometallic complex depends on many factors, including the nature of the complex and activator, the desired reaction rate, the kind of polyolefin product, the reaction conditions, and other factors. Generally, however, when the activator is an alumoxane or an alkyl aluminum compound, the amount used will be within the range of about 0.01 to about 500 moles, preferably from about 0.1 to about 300 moles, of aluminum per mole of M. When MAO is used, it is preferably used at a [Al:M] molar ratio of less than about 500, more preferably less than about 300. When the activator is an organoborane or an ionic borate or aluminate, the amount used will be within the range of about 0.01 to about 5000 moles, preferably from about 0.1 to about 500 moles, of activator per mole of M.

The ability to use low levels of an activator is a key advantage of the invention. As the examples below illustrate, MAO can be used at much lower levels than previously employed. While MAO is commonly used at [Al:M] molar ratios in the thousands (see U.S. Pat. No. 5,539,124 at Examples 16 and 22), I have now found that molar ratios as low as [Al:M]=200 or below can give catalysts with excellent activity when the complex is prepared as described herein. This is a valuable discovery because the activator is a major contributor to overall catalyst cost, and ways to reduce its use have long been sought by the industry.

Storage stability is another advantage of catalyst systems prepared by the method of the invention. As the results in Table 2 below confirm, aging has a dramatic negative effect on the activity of the catalysts made using the methods described in the '124 patent. In contrast, catalysts made by the method of the invention retain excellent activity, and polymers made using the catalysts of the invention have consistently narrow MWDs, even after 75 hours of storage.

If desired, a catalyst support such as silica or alumina can be used. However, the use of a support is generally not necessary for practicing the process of the invention.

Catalysts made by the method of the invention are particularly valuable for polymerizing olefins. Preferred olefins are ethylene and $C_3$–$C_{20}$ α-olefins such as propylene, 1-butene, 1-hexene, 1-octene, and the like. Mixtures of olefins can be used. Ethylene and mixtures of ethylene with $C_3$–$C_{10}$ α-olefins are especially preferred.

Many types of olefin polymerization processes can be used. Preferably, the process is practiced in the liquid phase, which can include slurry, solution, suspension, or bulk processes, or a combination of these. High-pressure fluid phase or gas phase techniques can also be used. The process of the invention is particularly valuable for solution and slurry processes.

The olefin polymerizations can be performed over a wide temperature range, such as about −30° C. to about 280° C. A more preferred range is from about 30° C. to about 180° C.; most preferred is the range from about 60° C. to about 100° C. Olefin partial pressures normally range from about 15 psig to about 50,000 psig. More preferred is the range from about 15 psig to about 1000 psig.

Catalyst concentrations used for the olefin polymerization depend on many factors. Preferably, however, the concentration ranges from about 0.01 micromoles per liter to about 100 micromoles per liter. Polymerization times depend on the type of process, the catalyst concentration, and other factors. Generally, polymerizations are complete within several seconds to several hours.

The following examples merely illustrate the invention. Those skilled in the art will recognize many variations that are within the spirit of the invention and scope of the claims.

EXAMPLE 1

Preparation of Bis(carbazolyl) Zirconium Dichloride

Carbazole (5.0 g, 30 mmol) is stirred in a flask under an atmosphere of nitrogen in a dry box for 15 min. Toluene (120 mL) is added, and the mixture is stirred for 30 min. n-Butyllithium (12 mL of 2.5 M solution in hexane, 30 mmol) is added by syringe over 5 min. to the stirred carbazole solution. The mixture is stirred at room temperature for 2 h. The mixture turns light pink, and the slurry becomes thick, requiring vigorous stirring. Zirconium tetrachloride (3.50 g, 15 mmol) and more toluene (25 mL) are added to the flask, and the mixture turns brown. Stirring is continued at room temperature for another 18 h, after which the mixture is black-brown-green. Solvents are removed under a flow of nitrogen, and the residue is vacuum dried for 3 h. A yellow solid (9.25 g), which contains the desired bis(carbazolyl) complex (about 36 wt. %) along with unreacted starting materials (about 50 wt. %) and some lithium chloride (about 3 wt. %) is isolated.

EXAMPLE 2

Ethylene Polymerization

A portion of the bis(carbazolyl) zirconium dichloride-containing mixture prepared in Example 1 (0.10 g) is dissolved in toluene (20 mL) in a small bottle and is stirred under nitrogen at room temperature for 30 min. The mixture has a concentration of bis(carbazolyl)zirconium dichloride in the solution of 0.0018 g/cm$^3$ (0.0036 mmol/cm$^3$). A sample of this mixture (0.5 mL) is used as the catalyst solution in the reaction described below. Ethylene, isobutane, and nitrogen are dried prior to use with 13X molecular sieves.

A 2-L stainless-steel reactor is preconditioned by heating it to 120° C. and maintaining that temperature for 20 min. under a flow of nitrogen.

Triisobutylaluminum (0.5 mL or 3.0 mL of a 0.9 M solution in heptane, 0.45 or 2.7 mmol; the amount used depends upon the moisture level of the feedstock and the reactor system) is charged to one side of a two-side injector. The other side of the injector is charged with the catalyst solution (0.5 mL), toluene (0 mL in this example), and methylaluminoxane (10% MAO in toluene, 2.18 M solution, product of Akzo Nobel, 0.165 mL, molar ratio of [Al:Zr]= 200).

1-Hexene (100 mL) is added to the reactor first. The triisobutylaluminum solution is then flushed into the reactor with isobutane (750 mL). The agitator is started, and the temperature controller is set to maintain a constant reactor temperature of 75° C.

The reactor is pressurized with ethylene to 400 psig. The catalyst/activator mixture is injected into the reactor along with more isobutane (50 mL) to initiate the polymerization. Ethylene is fed on demand using a Brooks mass flow meter to maintain a pressure of 400 psig in the reactor. The concentration of ethylene in the isobutane is about 13 mole %. The polymerization continues at 75° C. for 0.5 to 1 hour, and is then terminated by closing the ethylene feed valve and venting the reactor. The resulting polyethylene is collected and dried under vacuum at 50° C.

Catalyst activity: 150 kg/g Zr/h. Polymer properties: melt index:

0.11 dg/min.; MIR: 19; Mw/Mn: 2.49; density: 0.921 g/cm$^3$.

EXAMPLE 3

Ethylene Polymerization: Effect of Diluting Catalyst Solution

The procedure of Example 2 is followed, but the catalyst solution (0.5 mL) is diluted with 1.0 mL of toluene prior to adding it to the injector.

Catalyst activity: 310 kg/g Zr/h. Polymer properties: melt index: 0.12 dg/min.; MIR: 19; Mw/Mn: 2.52; density: 0.919 g/cm$^3$.

EXAMPLE 4

Ethylene Polymerization: Effect of Further Dilution

The procedure of Example 2 is followed, except that the catalyst solution has an intial concentration of 0.0009 g/cm$^3$ of bis(carbazolyl)zirconium dichloride (instead of 0.0018 g/cm$^3$) and 1.0 mL of this solution is added (rather than 0.5 mL), along with 1.0 mL of toluene, to the injector.

Catalyst activity: 460 kg/g Zr/h. Polymer properties: melt index: 0.14 dg/min.; MIR: 18; Mw/Mn: 2.45; density: 0.918 g/cm$^3$.

Comparative Example 5

Preparation of a Bis(carbazolyl) Zirconium Complex

The procedure of Example 16 of U.S. Pat. No. 5,539,124 is followed to prepare a bis(carbazolyl) zirconium complex. This procedure uses methylmagnesium bromide to deprotonate carbazole, and combines the resulting anion with 0.5 eq. of zirconium tetrachloride in ether at −78° C. After warming to room temperature, the mixture is stripped to remove ether. Toluene is added, and the mixture is filtered to remove insoluble material. The filtrate is then stripped to yield the bis(carbazolyl) complex.

Comparative Example 6

Ethylene Polymerization

The procedure of Example 2 is followed, except that the bis(carbazolyl) zirconium complex prepared in Comparative Example 5 is used.

Catalyst activity: 18 kg/g Zr/h. Polymer properties: melt index: 0.08 dg/min.; MIR: 25; Mw/Mn: 3.12; density: 0.925 g/cm$^3$.

Comparative Example 7

Effect of Dilution

The procedure of Example 3 is followed, except that the bis(carbazolyl) zirconium complex prepared in Comparative Example 5 is used.

Catalyst activity: 30 kg/g Zr/h. Polymer properties: melt index: 0.09 dg/min.; MIR: 25; Mw/Mn: 3.14.

Comparative Example 8

Effect of Further Dilution

The procedure of Example 4 is followed, except that the bis(carbazolyl) zirconium complex prepared in Comparative Example 5 is used.

Catalyst activity: 35 kg/g Zr/h. Polymer properties: melt index: 0.09 dg/min.; MIR: 25; Mw/Mn: 3.22.

Comparative Example 9

Ethylene Polymerization: Increased MAO Level

The data reported in Table 1 below for this example are obtained or calculated from Example 16 of U.S. Pat. No. 5,539,124, and are used herein as a comparison. Molar ratio of [Al/Zr]=8890; Catalyst activity: 134 kg/g Zr/h.

Comparative Example 10

Preparation of a Bis(carbazolyl) Zirconium Complex

The procedure of Example 22 of U.S. Pat. No. 5,539,124 is followed to prepare bis(carbazolyl) zirconium dichloride. This procedure reacts tetrakis(diethylamido)zirconium with carbazole followed by chlorination with silicon tetrachloride.

Comparative Example 11

Ethylene Polymerization

The procedure of Example 2 is used, except that the bis(carbazolyl) zirconium complex prepared in Comparative Example 10 is used.

Catalyst activity: 12 kg/g Zr/h. Polymer properties: melt index: 0.05 dg/min.; MIR: 29; Mw/Mn: 3.15.

Comparative Example 12

Effect of Dilution

The procedure of Example 3 is used, except that the bis(carbazolyl) zirconium complex prepared in Comparative Example 10 is used.

Catalyst activity: 20 kg/g Zr/h. Polymer properties: melt index: 0.06 dg/min.; MIR: 29; Mw/Mn: 3.21; density: 0.925 g/cm$^3$.

Comparative Example 13

Effect of Further Dilution

The procedure of Example 4 is used, except that the bis(carbazolyl) zirconium complex prepared in Comparative Example 10 is used.

Catalyst activity: 24 kg/g Zr/h. Polymer properties: melt index: 0.07 dg/min.; MIR: 30; Mw/Mn: 3.32; density: 0.925 g/cm$^3$.

Comparative Example 14

Ethylene Polymerization: Increased MAO Level

The data reported in Table 1 below for this example are obtained or calculated from Example 22 of U.S. Pat. No. 5,539,124, and are used herein as a comparison. Molar ratio of [Al/Zr]=1956; Catalyst activity: 10 kg/g Zr/h.

Comparative Example 15

Ethylene Polymerization using a Metallocene Complex

The procedure of Example 2 is followed, except that complex used is bis(n-butylcyclopentadienyl)zirconium dichloride, which is a conventional metallocene complex.

Catalyst activity: 147 kg/g Zr/h. Polymer properties: melt index: 0.11 dg/min.; MIR: 20; Mw/Mn: 2.82; density: 0.922 g/cm$^3$.

Comparative Example 16

Metallocene Complex: Effect of Dilution

The procedure of Example 3 is followed, except that bis(n-butyl-cyclopentadienyl)zirconium dichloride is used as the complex.

Catalyst activity: 230 kg/g Zr/h. Polymer properties: melt index: 0.11 dg/min.; MIR: 23; Mw/Mn: 2.76; density: 0.922 g/cm$^3$.

Comparative Example 17

Metallocene Complex: Effect of Further Dilution

The procedure of Example 4 is followed, except that bis(n-butyl-cyclopentadienyl)zirconium dichloride is used as the complex.

Catalyst activity: 240 kg/g Zr/h. Polymer properties: melt index: 0.12 dg/min.; MIR: 21; Mw/Mn: 2.74; density: 0.921 g/cm$^3$.

EXAMPLES 18 AND 19

Reproducible Catalyst Preparation

The procedure of Example 3 is repeated twice. The activity and polymer property results demonstrate the reproducibility of the catalyst preparation method:

Example 18: Catalyst activity: 305 kg/g Zr/h. Polymer properties: melt index: 0.11 dg/min.; MIR: 19; Mw/Mn: 2.44; density: 0.920 g/cm$^3$.

Example 19: Catalyst activity: 316 kg/g Zr/h. Polymer properties: melt index: 0.12 dg/min.; MIR: 19; Mw/Mn: 2.38; density: 0.919 g/cm$^3$.

Table 1 summarizes all of the results from the preceding examples. As the table shows, catalysts made by the method of the invention are much more active than bis(carbazolyl) zirconium complexes prepared as described in U.S. Pat. No. 5,539,124. In particular, the amount of MAO activator required for high activity is greatly reduced from a molar ratio [Al:Zr] of thousands to [Al:Zr] =200 (compare Example 2 with Comparative Examples 6 and 9). This is valuable because the activator is normally a major contributor to the cost of the catalyst system, and ways to reduce the amount needed are coveted by the industry.

Table 1 also illustrates the strong activating effect of solvents for catalyst systems of the invention. While the trend is the same in the prior-art catalysts, diluting catalysts of the invention increases activity threefold (see Examples 2–4) versus twofold for earlier bis(carbazolyl)zirconium catalysts (Comparative Examples 6–8 and 11–13). A weaker activating effect of dilution is also observed with a conventional metallocene, bis(n-butylcyclopentadienyl)zirconium dichloride (Comparative Examples 15–17).

In sum, when MAO is used as an activator at a molar ratio of [Al:Zr]=200, the catalyst systems of the invention are as active as the benchmark metallocene, bis(n-butylcyclopentadienyl)zirconium dichloride, and they are much more active than earlier bis(carbazolyl)zirconium complexes.

Table 1 also summarizes polymer properties. Polyethylene made using the catalyst systems has a favorable balance of properties, including good melt index and MIR, and narrow molecular weight distribution. In fact, the Mw/Mn values of polymers made using the catalyst systems of the invention, typically 2.4–2.5, are much narrower than those made from earlier bis(carbazolyl)zirconium complexes (3.1–3.3), and they are somewhat narrower than those of polymers made using bis(n-butylcyclopentadienyl) zirconium dichloride (2.7–2.8). Low densities are also easily achieved, which indicates that the 1-hexene comonomer is efficiently incorporated into the polymer.

Example 20 and Comparative Examples 21–23

Effect of Aging on Catalyst Activity and Polymer Properties zirconium catalyst of the invention (prepared in Example 1) is compared with bis(n-butylcyclopentadienyl)-zirconium dichloride and the catalysts prepared in Comparative Examples 5 and 10. A series of ethylene polymerizations is performed using the procedure of Example 3. Each of the four catalysts is aged in a dry box under nitrogen at room temperature for 1, 5, 10, 20, 30, 60, and 75 days prior to use in an ethylene polymerization. Table 2 summarizes the observed catalyst activities and polymer molecular weight distributions (Mw/Mn).

As the results in Table 2 indicate, aging has a dramatic negative effect on the activity of the catalysts made in Comparative Examples 5 and 10, which are made using procedures from U.S. Pat. No. 5,539,124. These catalysts would not polymerize ethylene at all with an activator (MAO) level of [Al:Zr] molar ratio=200 if the catalyst had been aged for 10 days or more. The results for Comparative Examples 21 and 22 are consistent with teachings in the '124 patent, which advises a skilled person to use this catalyst "as promptly as possible as it may lose some activity during storage."

In contrast, when a catalyst made by the method of the invention is used (Example 20), the catalyst retains excellent activity, even after 75 days of storage; no measurable amount of activity loss is observed. The metallocene control (Comparative Example 23) also retains its high activity after prolonged storage.

Also interesting is the impact of storage on polymer molecular weight distribution. Comparative Examples 21 and 22 show considerable broadening of molecular weight distribution over a few samples. On the other hand, the catalyst of the invention gives polymers with a consistently narrow Mw/Mn, even after 75 hours of storage; the metallocene control gives polymers with slightly broader Mw/Mn values, but ones that are also not very sensitive to aging.

EXAMPLES 24–30

Versatility of the Catalyst Preparation Method

The procedure of Example 1 is generally followed to make the 15 bis(carbazolyl), bis(8-quinolinoxy), and bis (indolyl) zirconium or titanium complexes listed in Table 3 (Examples 24–27) from zirconium tetrachloride or titanium tetrachloride. The starting materials for making the ligands are carbazole, 8-quinolinol, and indole. Each catalyst is used to polymerize ethylene using the process of Example 3. The results from these polymerizations appear in Table 3.

A similar method is used to make the indenylzirconium complexes (Examples 28–30), except that indenylzirconium trichloride is first prepared, followed by reaction with one equivalent of the anionic ligand precursor, which is made by deprotonating indole, carbazole, or 8-quinolinol with one equivalent of n-butyllithium. Each catalyst is used to polymerize ethylene using the process of Example 3. The results from these polymerizations appear in Table 3.

As shown in the table, the method of the invention is valuable for preparing a wide variety of complexes based on nitrogen-functional heterocyclic ligands. With a low level of MAO activator ([Al:M] molar ratio =200), each catalyst has good activity and incorporates 1-hexene well to produce low-density polymers.

The preceding examples are meant only as illustrations. The following claims define the invention.

TABLE 1

Ethylene Polymerization Results

| Ex. # | Catalyst | Source | MAO [Al:Zr] molar ratio | Conc. (g/mL) | Added (mL) | Toluene (mL) | Activity (kg/g Zr/hr) | MI (dg/min) | MIR | MWD | Density (g/mL) |
|---|---|---|---|---|---|---|---|---|---|---|---|
| 2 | bis(carbazolyl) Zr | Ex. 1 | 200 | 0.0018 | 0.5 | 0 | 150 | 0.11 | 19 | 2.49 | 0.921 |
| 3 | complex | | 200 | 0.0018 | 0.5 | 1 | 310 | 0.12 | 19 | 2.52 | 0.919 |
| 4 | | | 200 | 0.0009 | 1.0 | 1 | 460 | 0.14 | 18 | 2.45 | 0.918 |
| C6 | bis(carbazolyl) Zr | Comp. | 200 | 0.0018 | 0.5 | 0 | 18 | 0.08 | 25 | 3.12 | 0.925 |
| C7 | complex | Ex. 5 | 200 | 0.0018 | 0.5 | 1 | 30 | 0.09 | 25 | 3.14 | — |
| C8 | | | 200 | 0.0009 | 1.0 | 1 | 35 | 0.09 | 25 | 3.22 | — |
| C9 | | | 8890* | — | — | — | 134* | — | — | — | — |
| C11 | bis(carbazolyl) Zr | Comp. | 200 | 0.0018 | 0.5 | 0 | 12 | 0.05 | 29 | 3.15 | — |
| C12 | complex | Ex. 10 | 200 | 0.0018 | 0.5 | 1 | 20 | 0.06 | 29 | 3.21 | 0.925 |
| C13 | | | 200 | 0.0009 | 1.0 | 1 | 24 | 0.07 | 30 | 3.32 | 0.925 |
| C14 | | | 1956* | — | — | — | 10* | — | — | — | — |
| C15 | bis(n-butylcyclo- | | 200 | 0.0018 | 0.5 | 0 | 147 | 0.11 | 20 | 2.82 | 0.922 |
| C16 | pentadienyl) | | 200 | 0.0018 | 0.5 | 1 | 230 | 0.11 | 23 | 2.76 | 0.922 |
| C17 | zirconium dichloride | | 200 | 0.0009 | 1.0 | 1 | 240 | 0.12 | 21 | 2.74 | 0.921 |
| 18 | bis(carbazolyl) Zr | Ex. 1 | 200 | 0.0018 | 0.5 | 1 | 305 | 0.11 | 19 | 2.44 | 0.920 |
| 19 | complex | | 200 | 0.0018 | 0.5 | 1 | 316 | 0.12 | 19 | 2.38 | 0.919 |

*Values obtained or calculated from U.S. Pat. No. 5,539,124

TABLE 2

Effect of Aging on Catalyst Activity and Polymer Molecular Weight Distribution

| | | | Days Aged --> | | | | | | |
|---|---|---|---|---|---|---|---|---|---|
| Ex. | Catalyst | Source | 1 | 5 | 10 | 20 | 30 | 60 | 75 |
| | | | Catalyst Activity (kg/g Zr/h) | | | | | | |
| 20 | bis(carbazolyl) Zr complex | Ex. 1 | 310 | 290 | 297 | 310 | 315 | 300 | 320 |
| C21 | bis(carbazolyl) Zr complex | C. Ex. 5 | 30 | 12 | 0 | — | — | — | — |
| C22 | bis(carbazolyl) Zr complex | C. Ex. 10 | 20 | 8 | 0 | — | — | — | — |
| C23 | bis(n-BuCp)ZrCl$_2$ | | 230 | 230 | 240 | 235 | 240 | 235 | 230 |
| | | | Polymer Mol. Wt. Distribution (Mw/Mn) | | | | | | |
| 20 | bis(carbazolyl) Zr complex | Ex. 1 | 2.52 | 2.49 | 2.58 | 2.42 | 2.45 | 2.52 | 2.44 |
| C21 | bis(carbazolyl) Zr complex | C. Ex. 5 | 3.14 | 3.26 | — | — | — | — | — |
| C22 | bis(carbazolyl) Zr complex | C. Ex. 10 | 3.21 | 3.32 | — | — | — | — | — |
| C23 | bis(n-BuCp)ZrCl$_2$ | | 2.82 | 2.76 | 2.74 | 2.78 | 2.76 | 2.68 | 2.72 |

TABLE 3

Additional Ethylene Polymerization Examples

| Ex. # | Catalyst | MAO [Al:Zr] molar ratio | Conc. (g/mL) | Added (mL) | Toluene (mL) | Activity (kg/g M/hr) | MI (dg/min) | MIR | MWD | Density (g/mL) |
|---|---|---|---|---|---|---|---|---|---|---|
| 3 | bis(carbazolyl)ZrCl$_2$ | 200 | 0.0018 | 0.5 | 1 | 310 | 0.12 | 19 | 2.52 | 0.919 |
| 24 | bis(carbazolyl)TiCl$_2$ | 200 | 0.0018 | 0.5 | 1 | 348 | 0.03 | 25 | 3.45 | 0.924 |
| 25 | bis(8-quinolinoxy)ZrCl$_2$ | 200 | 0.0018 | 0.5 | 1 | 230 | 0.06 | 24 | 3.15 | 0.920 |
| 26 | bis(8-quinolinoxy)TiCl$_2$ | 200 | 0.0018 | 0.5 | 1 | 660 | 0.02 | 24 | 3.72 | 0.922 |
| 27 | bis(indolyl)ZrCl$_2$ | 200 | 0.0018 | 0.5 | 1 | 208 | 0.07 | 26 | 3.57 | 0.918 |
| 28 | Indolyl(indenyl)ZrCl$_2$ | 200 | 0.0018 | 0.5 | 1 | 260 | 0.35 | 24 | 4.03 | 0.917 |
| 29 | Carbazolyl(indenyl)ZrCl$_2$ | 200 | 0.0018 | 0.5 | 1 | 360 | 0.36 | 20 | 2.70 | 0.916 |
| 30 | 8-Quinolinoxy(indenyl)ZrCl$_2$ | 200 | 0.0018 | 0.5 | 1 | 255 | 0.42 | 19 | 3.48 | 0.919 |

I claim:

1. A method which comprises:
   (a) deprotonating a compound selected from the group consisting of indoles, carbazoles, 8-quinolinols, 2-pyridinols, and mixtures thereof, with an alkyllithium compound to produce an anionic ligand precursor; and
   (b) reacting the anionic ligand precursor with about 0.5 equivalents of a Group 4 transition metal tetrahalide at a temperature greater than about 10° C. in the presence of a hydrocarbon solvent to produce an organometallic complex-containing mixture.

2. The method of claim 1 wherein the ligand precursor is a carbazolyl anion.

3. The method of claim 1 wherein the alkyllithium compound is a $C_1$–$C_8$ alkyllithium compound.

4. The method of claim 1 wherein the alkyllithium compound is n-butyllithium.

5. The method of claim 1 wherein the Group 4 transition metal tetrahalide is selected from the group consisting of zirconium tetrachloride and titanium tetrachloride.

6. The method of claim 1 wherein step (b) is performed at a temperature within the range of about 15° C. to about 60° C.

7. The method of claim 1 wherein step (b) is performed at room temperature.

8. The method of claim 1 wherein one component of the mixture is an organometallic complex having the structure LL'MCl$_2$, wherein M is titanium or zirconium, and each of L and L', which may be the same or different, is selected from the group consisting of indolyl, carbazolyl, 8-quinolinoxy, and 2-pyridinoxy.

9. The method of claim 1 further comprising concentrating the product from step (b) without removing insoluble products.

10. An organometallic complex-containing mixture made by the method of claim 1.

11. An organometallic complex-containing mixture made by the method of claim 9.

12. A catalyst system which comprises:
   (a) an activator; and
   (b) the organometallic complex-containing mixture of claim 10.

13. A catalyst system which comprises:
   (a) an activator; and
   (b) the organometallic complex-containing mixture of claim 11.

14. A method which comprises:
   (a) deprotonating a compound selected from the group consisting of indoles, carbazoles, 8-quinolinols, 2-pyridinols, and mixtures thereof, with an alkyllithium compound to produce an anionic ligand precursor; and
   (b) reacting the anionic ligand precursor with about 1 equivalent of an indenyl Group 4 transition metal trihalide at a temperature greater than about 10° C. in the presence of a hydrocarbon solvent to produce an organometallic complex-containing mixture.

15. The method of claim 14 further comprising concentrating the product from step (b) without removing insoluble products.

* * * * *